United States Patent
Knappe et al.

(10) Patent No.: US 7,479,253 B2
(45) Date of Patent: Jan. 20, 2009

(54) METHOD OF ASSEMBLING A DIAGNOSTIC TEST STRIP HAVING A FUNCTIONAL OVERLAY

(75) Inventors: Wolfgang-Reinhold Knappe, Ludwigshafen (DE); Helmut Leininger, Mannheim (DE); Ralf Steinbrueck, Mannheim (DE); Franz Wittmann, Hockenheim (DE)

(73) Assignee: Roche Diagnostics GmbH, Mannheim (DE)

( * ) Notice: Subject to any disclaimer, the term of this patent is extended or adjusted under 35 U.S.C. 154(b) by 712 days.

(21) Appl. No.: 10/360,966

(22) Filed: Feb. 7, 2003

(65) Prior Publication Data
US 2003/0129086 A1    Jul. 10, 2003

Related U.S. Application Data

(63) Continuation of application No. 09/426,938, filed on Oct. 22, 1999, now Pat. No. 6,537,496.

(30) Foreign Application Priority Data
Oct. 23, 1998   (DE) ................. 198 49 024

(51) Int. Cl.
    *G01N 30/00* (2006.01)
(52) U.S. Cl. .................... 422/58; 422/50; 422/55; 422/56; 422/57; 422/68.1; 422/99
(58) Field of Classification Search ............ 422/58, 422/56, 50, 55, 57, 68.1, 99; 436/170, 177
    See application file for complete search history.

(56) References Cited

U.S. PATENT DOCUMENTS

| | | | |
|---|---|---|---|
| 3,802,842 A | 4/1974 | Lange et al. | |
| 4,312,834 A | 1/1982 | Vogel et al. | |
| 4,370,412 A | 1/1983 | Cruikshank et al. | |
| 4,732,849 A | 3/1988 | Seshimoto et al. | |
| 4,871,600 A | 10/1989 | Amann | |
| 5,228,847 A | 7/1993 | Lywood et al. | |
| 5,238,847 A | 8/1993 | Steinbiss et al. | |
| 5,262,067 A | 11/1993 | Wilk et al. | |
| 5,320,224 A | 6/1994 | Hauenstein et al. | |
| 5,536,470 A | 7/1996 | Frey et al. | |
| 5,846,837 A | 12/1998 | Thym et al. | |
| 6,055,060 A | 4/2000 | Bolduan et al. | |
| 6,537,496 B1 | 3/2003 | Knappe et al. | |

FOREIGN PATENT DOCUMENTS

| | | |
|---|---|---|
| AU | 702209 | 1/1998 |
| DE | 2118455 | 9/1972 |

(Continued)

*Primary Examiner*—Sam P Siefke
(74) *Attorney, Agent, or Firm*—Woodard, Emhardt, Moriarty, McNett & Henry LLP

(57) ABSTRACT

A flat-shaped functional overlay for at least one region of a flat-shaped flexible object which does not form a fold when the sandwich composed of the flexible object and overlay is bent towards the side on which the overlay is located is described. The overlay is composed of one or several flat-shaped overlays which are attached to the flexible object in such a way that a part of their surface can move freely relative to the surface of the object covered by this part in the direction of curvature produced when the object is bent.

In addition diagnostic test strips are described which have such an overlay.

5 Claims, 5 Drawing Sheets

FOREIGN PATENT DOCUMENTS

| | | |
|---|---|---|
| DE | 30 42 857 A1 | 5/1981 |
| DE | 40 15 589 A1 | 11/1993 |
| EP | 0 016 387 B1 | 1/1983 |
| EP | 0 291 843 B1 | 5/1988 |
| EP | 0 819 943 A2 | 1/1998 |
| EP | 0 821 233 B1 | 1/1998 |
| GB | 1276301 | 6/1972 |
| GB | 2291354 | 1/1996 |
| WO | WO 92/15879 | 9/1992 |

FIG. 13
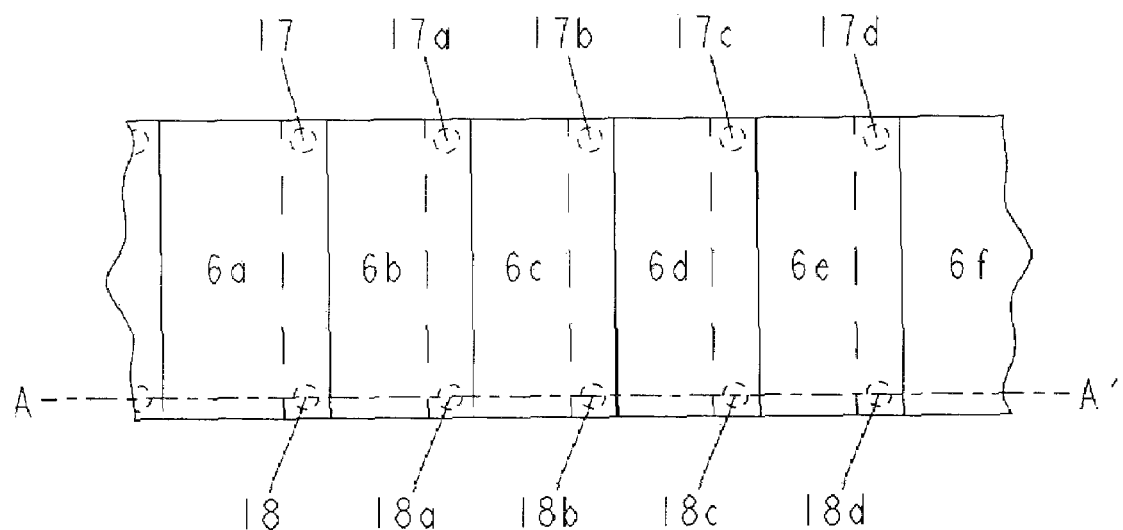
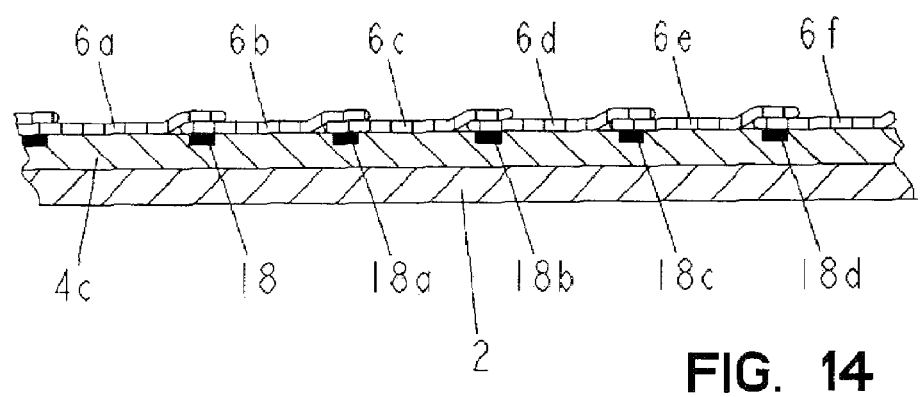
FIG. 14

METHOD OF ASSEMBLING A DIAGNOSTIC TEST STRIP HAVING A FUNCTIONAL OVERLAY

CROSS REFERENCE TO RELATED APPLICATIONS

The present application is a continuation of U.S. patent application Ser. No. 09/426,938 filed on Oct. 22, 1999, now U.S. Pat. No. 6,537,496, which claims the benefit of German Patent Application No. DE 198 49 024.0 filed on Oct. 23, 1998.

BACKGROUND OF THE INVENTION

The present invention concerns functional overlays which are not fastened over their whole surface and are attached to a flexible object in such a manner that they do not form a fold when the object is bent towards the side on which the overlay lies, and it concerns functional overlays to cover analyte-sensitive fields of test strips which ensure a uniform distribution of applied analyte-containing samples even when the test strips have more than a single detection field. The invention additionally concerns test strips which are furnished with such overlays and their use to determine diagnostically relevant analytes.

Functional overlays in the sense of this description of the invention are those which have a function without which the intended use of the object to which they belong would be impossible.

So-called carrier-bound tests are often used for the qualitative or quantitative analytical determination of components of body fluids in particular of blood. In these the reagents are present on or in corresponding layers of a solid test carrier which is contacted with the sample. The reaction of liquid sample and reagents leads to a detectable signal especially to a change in colour which can be evaluated visually or with the aid of an instrument, usually by reflection photometry.

Test carriers are frequently in the form of test strips which are essentially composed of an oblong support layer made of plastic material and detection layers mounted thereon as test fields. However, test carriers are also known which are designed as small quadratic or rectangular plates. In the following description the term "test strips" is also intended to encompass test carriers which do not have a strip shape.

Test carriers of the above-mentioned type are for example known from the German Patent document 21 18 455. This describes diagnostic test carriers for the detection of analytes in liquids which are composed of a support layer and at least one detection layer containing the detection reagents which is provided with a cover layer on its surface that does not adjoin the support layer. The cover layer can be composed of a fine-meshed network in the form of a fabric, knitted fabric or fleece. Plastic fabrics are stated as preferred networks in order to achieve a rapid wetting of the detection layer with sample liquid and to avoid interfering chromatographic effects. In order to detect an analyte in a liquid, such a diagnostic test carrier is dipped into a corresponding liquid preferably urine. In this manner the detection layer comes into contact with a very large excess of liquid which cannot be taken up by the test carrier. However, depending on the duration of contact of the detection layer with the liquid to be examined different colour intensities can be observed.

As a rule the results obtained are more positive the longer the contact time is. Therefore a correct quantitative analyte determination is not possible in this manner when there is a large excess of sample.

On the other hand a sample volume that is too small for a test carrier construction is a frequent cause for false measured values in diabetes monitoring i.e. the regular control of the blood of diabetics for the content of glucose.

Test carriers with the smallest possible volume requirement are therefore the goal of diverse current developments.

Diagnostic test carriers in the form of test strips which offer a considerable advance with regard to reproducibility of the test results even when different sample volumes are applied and with regard to hygienic handling are known from EP-A-0 821 233.

They contain a support layer with a detection layer arranged thereon containing reagents required to determine the analyte in a liquid sample and an overlay made of a network covering the detection layer which is larger than the detection layer and is attached to the support layer on both sides of the detection layer preferably via a spacer and in contrast rests directly on the detection layer without attachment i.e. essentially is in contact with the whole surface of this. The network used as an overlay should be hydrophilic but not alone be capillary active. An inert cover made of sample-impermeable material is arranged over the areas of the overlay which extend beyond the detection layer in such a manner that a sample application site remains free on the area of the network covering the detection layer.

In this construction the network covering the detection layer is preferably composed of high denier, relatively coarse-meshed monofilament fabric with an adequately large mesh size so that liquid can pass through the net onto the detection layer (page 3, line 12). In the example of this application a monofilament fabric with a mesh size of 280 μm is used. It has an important function: it rapidly passes sample liquid applied to its surface onto the underlying detection layer. When the detection layer is saturated a sample excess which may be present is led away into the boundary regions of the network which extend beyond the detection layer. In this manner small amounts of sample are made completely available to the detection layer but longer exposure to a sample excess which can lead to false-positive results is avoided.

An embodiment is also described in this document which has two or several detection layers arranged next to one another which are intended for the measurement of the same or different analytes.

The use of test carriers of this design of course at first sight offers tempting advantages with regard to work and cost savings since it should enable two or even several measurements to be carried out with a single application of sample. However, in practice various difficulties arise when it is attempted to use this design. An essential requirement that the required minimum sample volume of 6 μl for the measurement should not be exceeded cannot be fulfilled with such a test carrier construction in which the detection fields each have an area of about 20 to 40 mm$^2$ and the said network extends over both detection fields. It turns out namely that there is only a wetting of the test field above which the sample is applied. The second test field is not wetted even when sample volumes of up to 30 μl are applied. Even when the attempt to wet both test fields by placing the fields directly next to one another on the support without a gap does not lead to success. It turns out that even the tiny distance between the test fields of 5 to 10 μm which is still present in this case prevents blood from "jumping" from one to the other field.

Both test fields are only wetted when the sample is applied exactly over the gap between the two test fields. However, such an exact sample application is difficult to accomplish in practice. Although both test fields can be wetted when an application slit of only ca. 2 to 3 mm in width is left free in the inert cover above the network over the gap between the measurement fields a minimum sample volume of over 15 µl is required in this construction to completely wet the test fields.

It was found that the sample volume required for measurement can be reduced to ca. 4 µl when a functional overlay with a matched liquid distribution capacity (spreading capacity) preferably made of a thin textile material composed of low denier monofilaments or corresponding multifilament yarns is incorporated into the test construction instead of the high denier, coarse-meshed network.

Thin textile spreading fabrics, knitted spreading fabrics or spreading fleeces which have permeability, conductivity and capillary activity matched to the requirements of the individual case and usually have a low storage capacity are thus considerably more suitable than the high denier networks recommended in EP-A-0 821 233 especially for spreading low sample volumes over two or several different detection fields. It was also found that for perfect spreading of the analyte it is necessary that the spreading overlay should be in good contact with the base over which the spreading is to occur.

This requirement now results in a problem when using thin functional overlays which require a good contact with the underlying layer for perfect function if the test strips are inserted into a measuring instrument such as the well-known GLUCOTREND® instrument for evaluation in which it is placed under mechanical tension by bending to position it exactly. If the bending occurs towards the side on which the functional overlay according to the invention is located, then this has a tendency to form a fold in the area of the detection layer where the overlay rests free and unattached i.e. to lift up from the detection layer which considerably impairs or prevents the uniform filling of the detection layer. Especially in the case of test strips with two adjacent test fields a uniform supply to both test fields is prevented when the sample is applied.

BRIEF DESCRIPTION OF THE DRAWINGS

FIGS. 1 to 14 serve to illustrate the following embodiments.

FIG. 1 shows schematically a section through a section of a test strip with a thin functional overlay.

FIGS. 2 and 3 show schematically a section through a section of a test strip in a bent form provided with a thin functional overlay.

FIG. 4 shows schematically a section through a part of a test strip with a functional overlay attached according to the invention.

FIG. 5 shows the section of the object shown in FIG. 4 with the functional overlay attached according to the invention in a bent form.

FIG. 6 shows schematically a section through a part of a test strip with a functional overlay attached according to the invention.

FIG. 7 shows the section of the construction shown in FIG. 6 with the overlay elements attached according to the invention in a bent form.

FIG. 8 shows a perspective top-view,

FIG. 9 shows a section along the cutting line A-A',

FIG. 10 shows a top-view of the underside of an embodiment of a test strip according to the invention.

FIG. 11 shows a top-view of a section of a test strip,

FIG. 12 shows a transverse section along the cutting line A-A' of this object.

FIG. 13 shows a top-view of a part of a test strip with a series of detection fields which are covered by a series of shingle-like overlapping overlay elements according to the invention.

FIG. 14 is a sectional drawing along the cutting line A-A' of this object.

Figure 1:
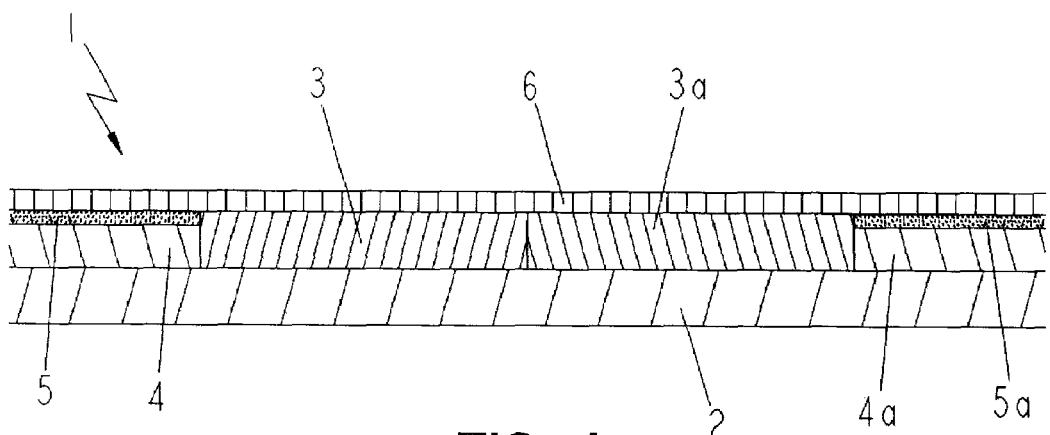

The reference numerals used in the figures have the following meaning:

| | |
|---|---|
| 1: | test strip |
| 2: | flexible carrier |
| 3 to 3d: | detection layers |
| 4 to 4c: | spacers |
| 5 and 5a: | adhesion layers |
| 6: | functional overlay according to the invention |
| 6a to 6f: | overlay elements according to the invention |
| 7: | attachment region |
| 8 and 8a: | movable region |
| 9: | arbitrary overlay |
| 10 and 10a: | protective cover |
| 11: | application area |
| 12 and 12a: | mark for the borders of the detection fields |
| 13: | mark for the direction of insertion |
| 14: | positioning hole |
| 15 and 16: | observation and measurement openings |
| 17 to 17d: | attachment points for the overlay elements |
| 18 to 18d: | attachment points for the overlay elements. |

DETAILED DESCRIPTION OF THE INVENTION

FIG. 1 shows schematically in a diagram that is not to scale for clearer illustration a section through a part of a test strip (1) which has two detection layers (3 and 3a) arranged directly adjacent to one another on a carrier (2) which are bordered by spacers (4 and 4a) on the right and left. An adhesion layer (5 and 5a) is applied to each of the spacers by means of which the thin functional overlay (6) which loosely rests on and spans the detection layer is fixed on both sides of the detection layers. The spacers together with the adhesion layer expediently have approximately the same thickness as the detection layers. The step which may be present between the surface of the adhesion layer facing the overlay and the detection layers should be so small that it does not significantly impair whole area contact between the overlay and the detection layers.

The attachment of the detection layers and the spacers on the carrier which is of course present which can also be achieved by adhesion layers is not shown in the figure.

Figure 2:
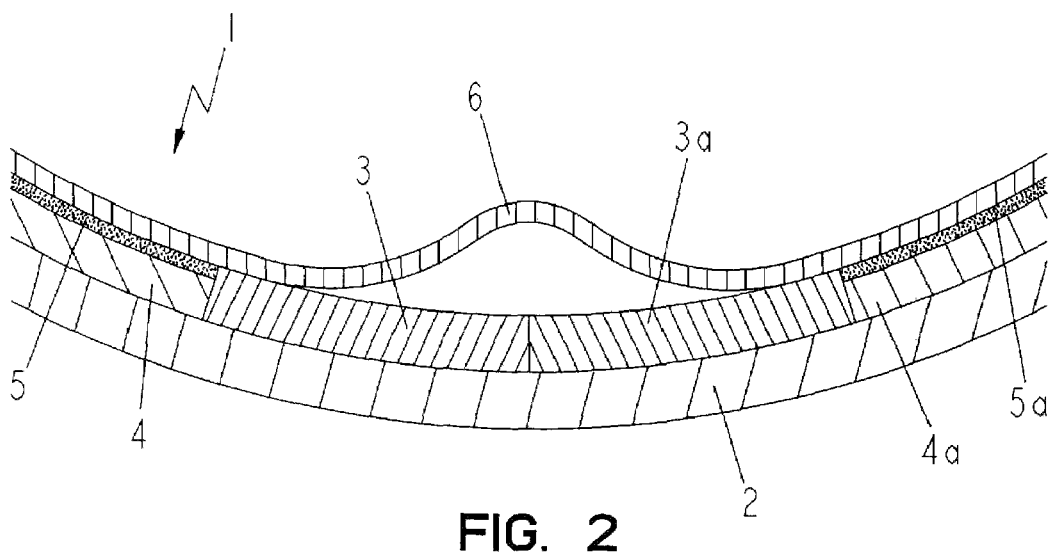
Figure 3:
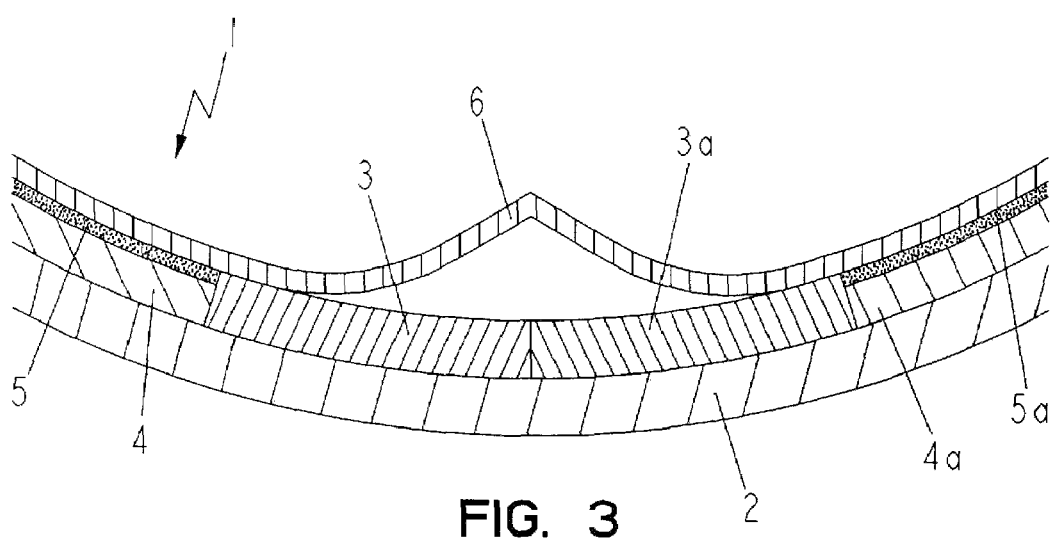

FIGS. 2 and 3 show schematically in a diagram that is not to scale for clearer illustration and with an exaggerated bending a cross-section through a section of a test strip (1) provided with a thin functional overlay as already illustrated in FIG. 1 which was bent towards the side on which the overlay is attached.

The test strip (1) has two detection layers (3 and 3a) arranged directly adjacent to one another on a carrier (2) which are bordered by spacers (4 and 4a) on the right and left. An adhesion layer (5 and 5a) is applied to each of the spacers by means of which the overlay (6) is attached on both sides of the detection layers. It can be seen that the bending has lifted a large area of the overlay from the detection layers and has formed a fold the shape of which naturally depends among others on the flexural rigidity, the construction compressibility and homogeneity of the overlay material.

The object was therefore to find a construction which avoids the formation of folds in the area of bending of the test strip despite using an overlay made of a relatively thin overlay material which in principle is able to supply optionally several test fields uniformly with sample material from one application point. To generalize this means finding a construction which enables an overlay which is not attached over its entire surface to be mounted on a flexible support such that when the sandwich is bent towards the side on which the overlay is located no fold is formed in the latter even in the unattached region of the surface.

When flat-shaped, not very thin, flexible objects which are composed of a sandwich of several layers are bent, the layers on the inner side of the bend are compressed and the layers lying on the outside are stretched. If the layer on the inside of the bend in such layer systems is not joined over its complete area to the other layer or layers, but only at spaced points, then this layer has a tendency to evade the force of compression by forming folds at the regions of the surface which are not firmly attached to the surface of the object. Hence the formation of folds is a consequence of the "principle of least constraint" which is always effective in nature which the sought-after construction should be able to overcome.

This object is achieved according to the invention by a flat-shaped functional overlay for at least a region of a flat-shaped flexible object which does not form a fold when the sandwich composed of the flexible object and overlay is bent towards the side on which the overlay is located which is characterized in that it is composed of one or several flat-shaped overlays which are attached to the flexible object in such a way that at least a part of their surface can move freely relative to the surface of the object covered by this part in the direction of curvature produced when the object is bent.

An overlay element of the overlay according to the invention is attached to the flexible object by at least one, preferably at least two, attachment points which are in a connected surface area (attachment region) of the overlay element which extends between the edges of the overlay element lying in the direction of curvature and whose boundary to the freely movable part of the overlay element is essentially a straight line and at right angles to the direction or curvature.

Figure 4:
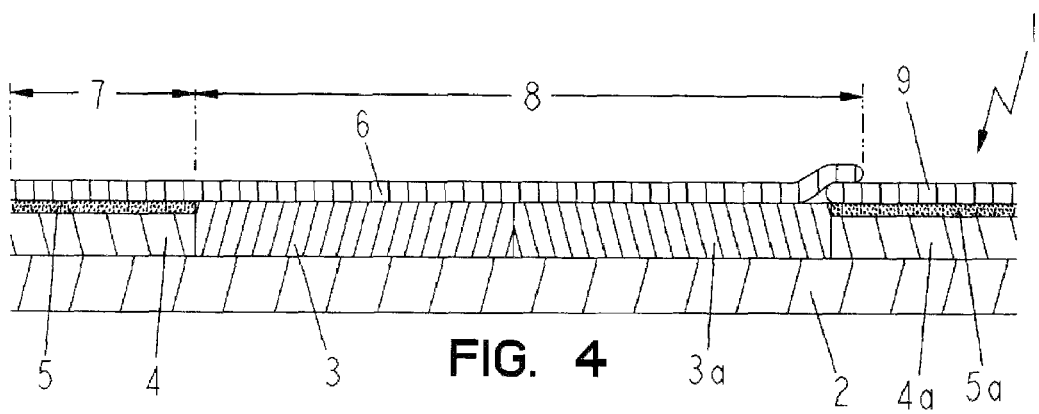

FIG. 4 shows schematically in a diagram that is not to scale for clearer illustration a cross-section through a section of an object containing a functional overlay attached according to the invention which is again to put it in concrete terms in the shape of a test strip (1) which has two detection layers (3 and 3a) located directly next to one another on a support (2) which is bordered on the left side by a spacer (4). An adhesion layer (5) is applied to the spacer by means of which one side of the overlay (6) according to the invention is attached in its attachment region (7). The cover region (8) which can move freely in the direction of curvature of the overlay (6) rests loosely on top and covers the detection layer and its free end overlaps with an arbitrary overlay (9) which in turn is attached over its entire area on the support by means of a spacer (4a) having an adhesion layer (5a). The thickness of the structure composed of overlay (9), spacer (4a) and adhesion layer (5a) corresponds to the thickness of the detection layers in this diagram. The spacers (4) together with the adhesion layer (5) expediently have about the same thickness as the detection layers.

Figure 5:
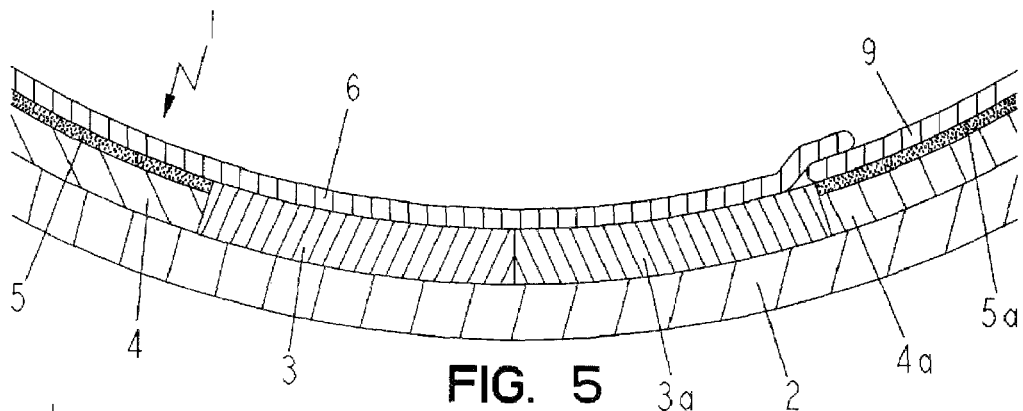

FIG. 5 shows the cross-section of the object shown in FIG. 4 with the functional overlay attached according to the invention in a bent form. It can be seen that in this case the overlay (6) does not form a fold despite the bending but rather the entire region of overlap rests on the detection layers (3) and (3a). As a result its overlap with the overlay (9) has increased by displacement of the slidable end of the overlay (6) according to the invention in the direction of curvature.

Hence each overlay element is divided into an attachment region and into a cover region which can slide over the object. The border between the regions extends essentially at right angles to the direction of curvature of the flexible object.

A possible division of a rectangular overlay element into a slidable region and an attachment region is for the attachment region to comprise one end and the slidable region to comprise the other end of the overlay element, the border between both regions running parallel to one edge at right angles to the direction of curvature of the flexible object.

Of course the overlay element can also be attached in a strip-shaped region in the middle of the element such that both ends can slide freely on the object.

There are in principle no constraints on the relative sizes of the areas of the attachment region and slidable region. The size of the areas depends on the special requirements of the individual case. The size of the attachment region must be sufficient to ensure a secure attachment but it can also be considerably enlarged if this is desired for special functions. The area of the slidable overlay region and especially its extension towards the curvature depends on the stiffness of the overlay material, the expected degree of curvature and of course on the size of the area to be covered by the overlay. If the curvature is expected to be low, the extension in the direction of curvature can be larger than with tighter bends. The expedient length of the slidable overlay region for a planned application can be most simply determined by a few systematic experiments.

A simple, potential and expedient type of attachment especially when only one overlay element is used is to fix the whole area of the attachment region of the overlay element to the flexible object as shown in FIGS. 4 and 5.

In order to completely cover the object or to completely cover the region to be covered of the object despite different movements of the slidable part of the overlay element when there are different curvatures, it is expedient that the slidable end of the overlay overlaps with an overlay having the same or any other type of attachment or with any other cover of the region of the object to be covered as shown in FIGS. 4 and 5.

If two overlay elements are necessary and sufficient to cover the region to be covered of the flexible object, this overlap can be achieved in an elegant manner by attaching both overlay elements to the object in such a way that their slidable regions face each other and overlap.

Figure 6:
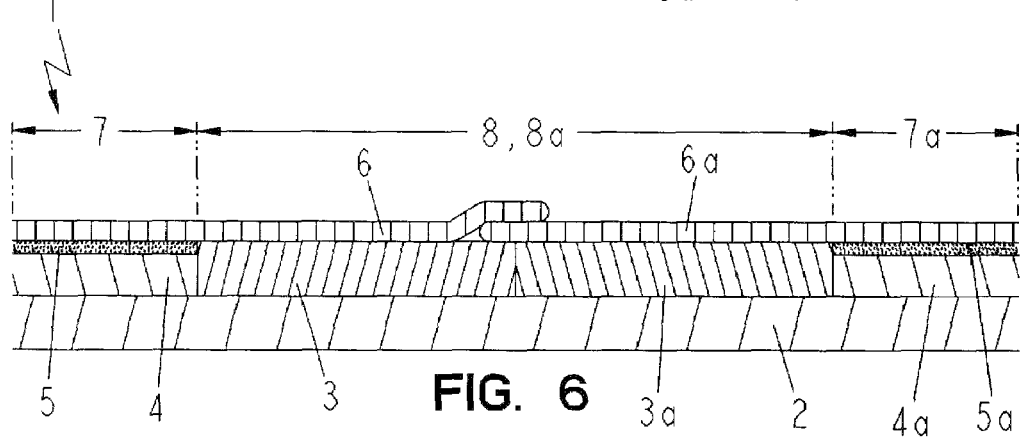

FIG. 6 illustrates this construction: It shows schematically in a diagram that is not to scale for clearer illustration a cross-section through a section of an object containing a functional overlay attached according to the invention which is again in the shape of a test strip (1) to put it in concrete terms which has two detection layers (3 and 3a) located directly next to one another on a support (2) which are bordered left and right by spacers (4 and 4a). Adhesion layers (5 and 5a) are applied to the spacers by means of which one side of each of the overlays (6 and 6a) according to the invention are attached in their attachment regions (7 and 7a). The regions (8 and 8a) of the overlay which can slide freely in the direction of curvature cover and rest loosely on the detection layer and overlap each other at their free ends. It is expedient that the spacers together with the adhesion layer have approximately the same thickness as the detection layers.

Figure 7:
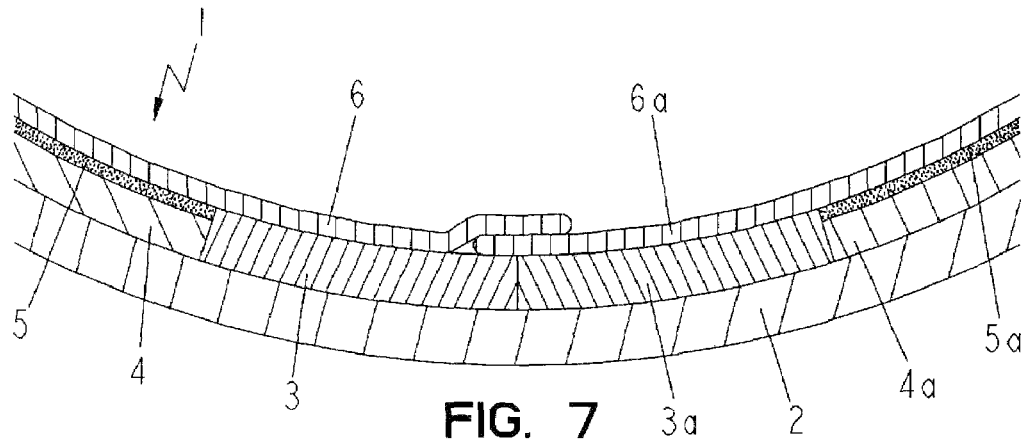

FIG. 7 shows the cross-section of the construction shown in FIG. 6 with the functional overlay elements attached according to the invention in a bent form. It can be seen that in this case the overlays (6 and 6a) do not form a fold despite the bending but rather the entire region of overlap rests on the detection layers (3) and (3a) without a gap. The very slight lifting of the overlay element (6) directly in front of the overlap with the overlay element (6a) does not interfere with the sample distribution on the detection layers.

In practice it has turned out that it is sufficient when the overlay elements overlap over a length of 0.5 to 2.5 mm.

Although initially the object of the invention was only to attach relatively thin spreading overlays which are suitable for evaluating small sample volumes onto test strips in such a way that they remain in whole area contact with the detection layer(s) even when the test strip is bent, the invention is not limited to the solution of this special problem. On the contrary the inventive manner of attachment recommends itself for all functional overlays whose practical function is based on the use of an unattached contact which is, however, as unbroken as possible i.e. a whole area contact with a flexible support if the support may bend during its use.

The inventive type of attachment makes a very valuable contribution to reliable use especially for test strips whose correct function is particularly important and must be ensured under various conditions of use and when used by laymen with various degrees of skill. Its use for test strips is therefore also a subject matter of the invention and has been shown above in the figures as illustrative examples of the invention.

The invention is a great help in the manufacture of test strips in which a very small amount of blood should be distributed uniformly over relatively large and optionally several test areas. For example a requirement for such test strips is that ca. 5 µl blood should be distributed over a test area of 30 to 40 mm² which may optionally be subdivided.

Functional overlays are preferably used in such test carriers to cover at least partial areas and especially the detection layers of test carriers which are characterized in that they are composed of an open pore flat-shaped structure made of a textile material which is itself not capillary active but permeable to liquids and its construction and material and/or hydrophilizing finish are selected such that it spreads 10 µl of water over an area of more than 300 mm² when resting on a support.

Textile fabrics which fulfil this requirement may be found among commercial materials. Suitable textile materials can be basically initially selected according to the motto as thin as possible with a weight per unit area which is as small as possible. The following spreading test can be used for the fine selection of suitable materials.

10 mm wide and at least 100 mm long strips of the textile material to be examined which may optionally have a hydrophilic finish are placed on the matted side of a polycarbonate foil. Then 10 µl water is applied as a spot to the middle of the strip and its spreading is observed. With a suitable material the spreading process should be completed within 5 to 10 seconds and the wetted area should be at least 30×10 mm.

This test can for example be used to demonstrate the major differences between the polyester fabric PE 280 HC used according to EP-A-0 821 233 as a spreading material and the textile materials used according to the invention e.g. the polyester fabric PE 38 HC or Viledon fleece material FO 2451/121 as follows:

10 mm wide strips of the textile materials to be tested are impregnated with the same amount (ca. 0.25% by weight relative to the material weight before impregnation) of sodium-N-oleoyl sarcosinate and dried. Then the impregnated textile strips are placed on the matted side of a polycarbonate foil. If 10 µl water is then applied as a spot, the water spreads in 5 to 10 seconds over the areas stated in the following table and then comes to a standstill:

| According to | Material | Area |
|---|---|---|
| EP-A-0821233 | PE 280 HC | 8 × 10 mm |
| invention | PE 38 HC | 40 × 10 mm |
| invention | Viledon OF 2451/121 | 50 × 10 mm |

Fabrics, knitted fabrics or fleeces with a thickness of 20 to 200 µm, preferably of 30 to 100 µm and/or a pore volume of 30 to 85, preferably of 40 to 75% have proven to be particularly suitable as textile materials for spreading small amounts of blood. The weight per unit area of these particularly suitable materials for spreading small sample volumes is 10 to 200, preferably 10 to 50 g/m².

In this connection materials with thicknesses below 100 µm in particular below 50 µm and weights per unit area of below 50 and preferably below 25 g/m² are particularly preferred.

Particularly preferred flat-shaped structures with the said dimensions are fabrics and fleeces. Preferred fabrics are those which have a mesh size below 200 µm, preferably of 20 to 150 µm in particular of 20 to 60 µm, are slip-resistant and are manufactured from monofilaments with deniers in the range of 2 to 20 dtex, preferably 4 to 15 dtex in a linen weave. The fabrics can also have a slip-resistant finish applied after weaving. However, the slip-resistance of the fabric is preferably achieved by impressing a wave-like deformation on the monofilaments during the fabric manufacture and/or by slightly melting together the warp and weft filaments at the crossing points which secures them against slipping.

Fleeces used according to the invention are random fleeces preferably spun-bonded fleeces. They are composed of continuous monofilaments with a denier in the range of 0.5 to 2.5 dtex, preferably of 0.8 to 2.0 dtex. The bonding can be carried out by treating the fleeces with bonding agents; however, autogenic bonding is preferred in which the filaments are gently melted together at their crossing points. The pores of such fleeces inherently have considerable size differences. Surprisingly fleeces with the features stated above are outstandingly suitable for the inventive use despite the large variation in pore size.

The slight or absent capillary activity of the flat-shaped structure is exhibited by the fact that it has a height of rise of water at 25° C. of less than 2 mm in 10 sec.

Fibre materials that come into consideration for the textile materials to be used according to the invention are natural fibres such as cellulose or protein fibres, semisynthetic fibres such as acetate or viscose silk or completely synthetic fibres such as polyester, polyamide, polyurethane or polyacrylonitrile, poly-ethylene or polypropylene fibres or mixtures of the said fibre types.

Preferred cellulose fibres are cotton fibres, preferred protein fibres are wool and natural silk. Suitable acetate fibres are 2,5- or triacetate fibres depending on the desired degree of hydrophilicity. Preferred synthetic fibres are composed of polyethylene terephthalate, polyamide-6, polyamide-6,6 or modified polyacrylonitrile.

Synthetic and in particular thermoplastic fibres are preferred over natural fibres due to their high resistance to environmental influences and the possibility of modifying mechanical and chemical properties according to need during their manufacture.

The functions exercised by the overlays and especially the spreading function requires that the fibre materials of the overlays are wetted by the liquids that are to be spread by them.

This wettability is not usually present by nature when using completely synthetic fibres and in particular those made of unpolar monomers if the liquid phase i.e. the analyte solution to be examined is essentially aqueous. In these cases it is expedient to hydrophilize the fibre materials.

For the hydrophilization they can for example be treated with a surface-active material such that an active coating of the surface-active material is deposited on the fibres of the textile material.

N-acyl-N-alkylglycinates of formula I are preferred for the hydrophilization of overlays according to the invention made of hydrophobic fibres

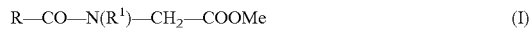

$$R-CO-N(R^1)-CH_2-COOMe \qquad (I)$$

in which R denotes an aliphatic residue with 9 to 23 C atoms in particular 11 to 17 C atoms which is saturated and has one to three double bonds, $R^1$ denotes hydrogen or lower alkyl and Me is hydrogen or a metal atom.

R is in particular the aliphatic chain of lauric acid, myristic acid, palmitic acid, stearic acid or palmitoleic acid, oleic acid (olein), linoleic acid, linolenic acid and isomers thereof.

The use of an N-acyl-N-alkylglycinate mixture is also very advantageous in which the structure and proportion in the mixture of the residues R corresponds to the structure and abundance of the alkyl residues of natural fatty acids e.g. tallow fat or coconut fatty acid. In technical usage such alkyl mixtures are for example referred to as "tallow fatty alkyl" or "coconut fatty alkyl".

Lower alkyl groups representing $R^1$ are preferably linear and have 1 to 4, in particular 1 or 2 C atoms. A methyl group is particularly preferred for $R^1$.

The metal atom Me is expediently selected such that the glycinate of formula I is water-soluble. In particular alkali metals preferably sodium and potassium are suitable.

Sodium oleoyl-sarcosinate is mentioned as an example of a particularly preferred compound of formula I for the hydrophilization of overlays according to the invention.

In order to achieve a hydrophilically active coating on overlay materials according to the invention an amount of 0.01 to 2% by weight, preferably of 0.03 to 0.5% by weight, of the glycinate relative to the weight of the overlay material before impregnation is usually adequate.

Alternatively overlays which are by nature hydrophobic can be vapour-coated with a readily oxidizable metal or semi-metal such as with Al, Si, Ti, V, Cr, Mn, Fe, Co, Ni, Zn, Ga, Ge, Zr, Nb, Cd, In, Sn or Sb, preferably with Al, Si, Ti or Zr and especially with Al and this is subsequently oxidized to form a hydrophilic oxide film as proposed in the German patent application No. 19753848.

Commercial textile sheet materials which can be used according to the invention especially after a hydrophilization are for example the monofilament polyester fabric type PE nn HC or the monofilament nylon fabric type NY nn HC or HD from the ZBF Mesh+Technology Company, Rüschlikon, Switzerland in which nn varies from 20 to 150, in particular the polyester fabric type PE 38 HC or the monofilament nylon fabric type NY 41 HC. The Viledon® fleece materials FO 2451, in particular type FO 2451/121 from the Freudenberg Company, Weinheim, Germany are very well suited for use according to the invention.

Of course all textile sheet materials are also suitable as the functional overlay according to the invention which have the above-mentioned structural features and have a pronounced spreading effect due to their material properties or alternative finishing treatments to those already mentioned such as corona plasma treatment, a plasma chemical vapour deposition or coating with nano-composites.

Functional overlays according to the invention are constructed within the framework of the stated parameters such that they remain in contact with the detection layers without being attached all over. As described above they are only fixed on the support outside the detection layer expediently by means of a spacer. In contrast to the teaching known from DE-A-30 42 857 (page 10) for the manufacture of test strips they are not pressed into the detection layers or bonded with them. Such a permanent bond makes the described spreading function impossible.

The functional overlays according to the invention have very favourable spreading properties i.e. they are extremely suitable for the uniform distribution of liquid analyte samples on detection layers. As a result of their expedient combination of permeability and liquid conducting capacity they are considerably superior to previously described overlays and covers and as a result they are even able to supply several adjacent detection areas uniformly with sample material from one application point.

Hence the test strips provided with the functional overlay according to the invention can therefore advantageously be used for the simultaneous determination of several different analytes on adjacent detection fields in which case the minimal sample quantity is below 10 µl, typically in the range of 4 to 6 µl, an excellent uniform distribution of the sample on the different detection fields occurs and a several-fold excess of sample is not detrimental. It has namely turned out that when a test strip is used which has been constructed using the above-mentioned preferred materials, a sample excess is not taken up by the strip but rather remains above the application site. A further major advantage of the constructions according to the invention is that the test strips are self-dosing. If its application site is brought into contact with a blood drop standing on or hanging from the finger pad the strip only takes the amount that is required to saturate the detection layer(s) the remainder remains on the finger.

The invention also concerns a process for the construction of a flat-shaped functional overlay for at least one region of a flat-shaped, flexible object the whole area of which is not attached to the object and does not form a fold when the sandwich composed of the flexible object and overlay is bent towards the side on which the overlay is located which is characterized in that a flat-shaped overlay element or several overlapping flat-shaped overlay elements together form the overlay, are attached to the flexible object in such a way that a part of its/their surface can move freely relative to the area of the object covered by this part in the direction of curvature created by bending the object.

In this process it is preferable to use flat-shaped overlay elements which are composed of one of the above-mentioned preferred textile materials.

It is particularly preferable to use flat-shaped overlay elements which are hydrophilized with an N-acyl-N-alkyl-glycinate of formula I.

In addition to the functional overlay according to the invention with the described attachment according to the invention especially in combination with the above-mentioned overlay materials and the preferred hydrophilizing finish, a test strip is also a subject matter of the present invention composed of a flexible flat-shaped support on which one or several test fields are arranged next to one another which each carry one or several detection layers stacked on top of one another which is characterized in that the test fields are covered by a functional overlay described above according to the invention which rests loosely on them and is attached to the support in the manner according to the invention.

Test strips according to the invention should preferably be used for diagnostic purposes and preferably have at least two directly adjacent single or multilayer test fields for the same or different analytes whereby in practice a microscopic gap of ca. 5-10 µm is also present in this case, or two single layer or multilayer test fields separated by a gap for the same or different analytes.

The detection layers applied to the test fields contain reagents for the detection of a diagnostically utilizable analyte. The detection of the same analyte on two separate test fields may be of interest when the purpose of the detection layers is to enable a qualitative, semi-quantitative or quantitative assessment of very different concentrations of the analyte or if simply an assessment of the reproducibility of the measured result is desired. Of course the case is of particular interest where both detection layers enable the simultaneous qualitative detection or a semiquantitative or quantitative determination of two different analytes and especially those which can be used diagnostically.

It is particularly practical, especially when the test strip has two test fields when they are covered by an overlay according to the invention of the type described above and illustrated in FIG. 6 in which the test fields are covered by two overlay elements which are attached to the test strip in such a manner that their displaceable regions face each other and overlap. In this case an optimal distribution of the sample is achieved when the overlap of the two overlay elements is located over the separating line between the two test zones and is preferably symmetrical thereto.

In this case the overlay elements are attached over the whole area of the attachment region.

The test fields are preferably mounted on the test carrier one behind the other in the direction of its longitudinal axis and the overlay elements, viewed in the same direction, are attached in a zone on the flexible support which is located in front of and behind the test fields.

In addition it is preferred that the overlay elements are attached to spacers which have approximately the thickness of the detection layers.

Finally it has proven to be expedient when the arrangement of detection layers and overlays on the test strip is covered with an inert flat-shaped material in such a manner that a space only remains free that is adequate for sample application in the overlay region of the overlay elements which is usually 2 to 5 mm viewed in the direction of the longitudinal axis of the test strip.

The support of the test strip is composed of a transparent material and/or has cut-outs in the region of the test fields of the same or different shape through which the underside of the detection layers can be inspected. It is advantageous especially for an automation of the test evaluation when the support of the test strip has adjustment marks in the form of additional holes, cut-outs or notches.

Figure 8:
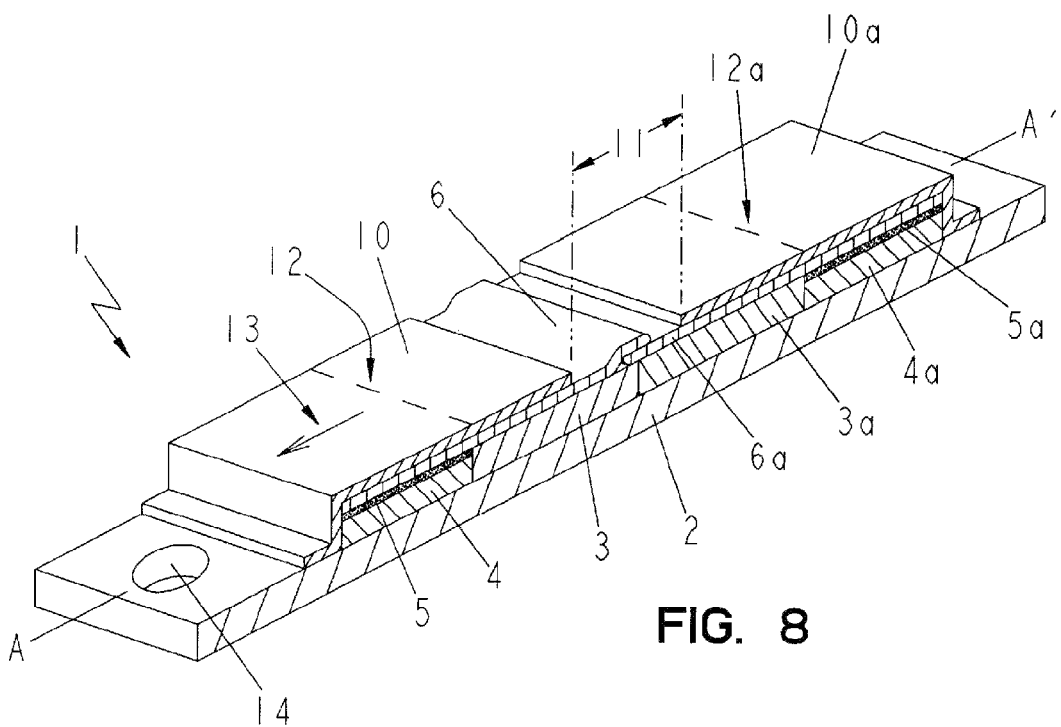
Figure 9:
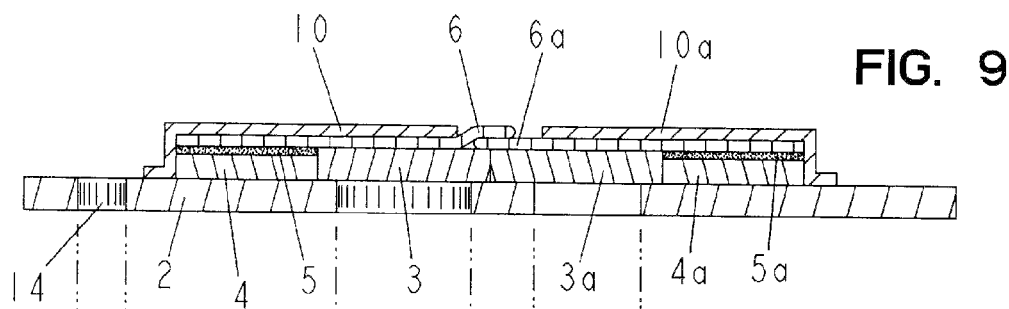
Figure 10:
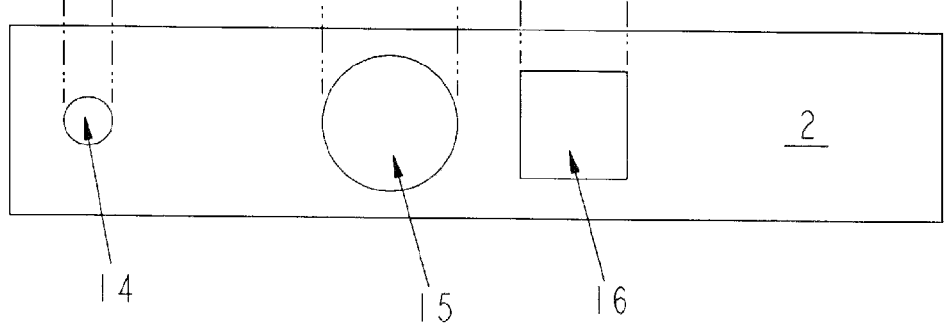

FIG. 8 shows a perspective top-view, FIG. 9 shows a section along the cut line A-A' in FIG. 8, FIG. 10 shows a top-view of the underside of an embodiment of a test strip according to the invention with two directly adjacent detection areas and an overlay according to the invention in an attachment according to the invention. This representation is also not to scale in order to make the construction clearly visible. A concrete dimensioning of this embodiment can be derived from the practical example.

The diagnostic test carrier (1) according to the invention shown perspectively in FIG. 8, in section in FIG. 9 and from below in FIG. 10 has the shape of a test strip. Two detection layers (3, 3a) that are directly adjacent and covered by the overlay elements (6, 6a) are located on a support layer (2). The overlay elements (6, 6a) are attached to the support layer (2) next to the detection layers (3, 3a) by means of spacers (4, 4a) and adhesion layers (5, 5a). These spacers can in practice also be hot-melt adhesive areas or double-sided adhesive tapes which fix the overlays (6, 6a) on the support layer (2). Ideally the spacers together with their adhesive surfaces have approximately the same thickness as the detection layers (3, 3a). The construction shown here additionally has covers (10, 10a) which are attached to the support layer (2) and to the overlay elements (6, 6a). They are arranged in such a way that they cover the regions extending beyond the detection layers (3, 3a) and a part of the area of the overlays (6, 6a) resting on the detection layers. However, they only leave the overlapping region of the overlay elements (6, 6a) located above the border of the detection zones free. This region is the sample application site (11). The sample liquid to be examined is applied to this. If the covers are transparent markings (12, 12a) may be applied to them over the external limits of the detection fields which enable the user to recognize when the detection fields are completely saturated with sample liquid. If this is the case then the sample quantity was adequate, otherwise it may be suspected that the amount of sample was too small and that possibly the measurement was erroneous. The left cover (10) contains printed arrows (13) which show the user which end of the test carrier (1) he should place or insert into a measuring instrument. The positioning hole (14) serves to hold the test strip, in the case of a measurement by an apparatus such as by reflection photometry, at an exactly predetermined position of the apparatus. This can for example be achieved in that for example a pin extends into the positioning hole (14) and in this manner fixes the test carrier (1) at a predetermined position.

FIG. 10 shows the underside of the test strip according to the invention containing the positioning hole (14) placed in the support (2) and the differently shaped observation openings (15 and 16) through which the detection layers can be inspected and measured.

In a diagnostic test carrier according to the invention materials which come into particular consideration for the support layer are those which do not take up the liquids to be examined. These are so-called non-absorbent materials of which plastic foils for example made of polystyrene, polyvinylchloride, polyester, polycarbonate or polyamide are particularly preferred. However, it is also possible to impregnate absorbent materials such as wood, paper or cardboard with water-repellent agents or to coat them with a water-resistant film where silicone or hardened fats can be used as hydrophobizing agents and for example nitrocellulose or cellulose acetate can be used as film formers. Metal foils or glass are suitable as additional support materials.

In contrast for a detection layer it is necessary to use materials which are able to take up the liquid to be examined together with the components contained therein. These are so-called absorbent materials such as fleeces, fabrics, knitted fabrics, membranes or other porous plastic materials or swellable materials such as gelatin or dispersion films which can be used as layer materials. Materials which can be used for the detection layer must of course also be able to carry reagents that are necessary to detect the analyte to be determined. In the simplest case all reagents required for the detection of the analyte are on or in one layer. However, cases are also conceivable where it is more advantageous to divide the reagents over several absorbent or swellable material layers which can then be arranged above one another and in whole area contact. The term "detection layer" used in the following is intended to encompass those cases in which the reagents are either located only in or on one layer or in two or even several layers as described above.

Preferred materials for the detection layer are papers or porous plastic materials such as membranes. Of these asymmetric porous membranes are particularly preferred which are preferably arranged such that the sample liquid to be examined is applied to the large-pored side of the membrane and the analyte is determined on the fine-pored side of the membrane. Particularly preferred porous membrane materials are polyamide, polyvinylidene difluoride, polyethersulfone or polysulfone membranes. Polyamide 66 membranes and hydrophilized asymmetric polysulfone membranes are outstandingly suitable. The reagents for the determination of the analyte to be detected are usually incorporated into the aforementioned materials by impregnation or are applied to one side by coating. When coating asymmetric membranes it is preferable to coat the fine-pored side.

However, so-called open films also come into consideration for the detection layer as described for example in EP-B-0 016 387. For this solids in the form of fine insoluble organic or inorganic particles are added to an aqueous dispersion of film forming organic plastics and the reagents required for the detection reaction are additionally added. Suitable film formers are preferably organic plastics such as polyvinyl esters, polyvinyl acetates, polyacrylic esters, poly-methacrylic acid, polyacrylamides, polyamides, poly-styrene, mixed polymers for example of butadiene and styrene or of maleic acid ester and vinyl acetate and other film-forming natural or synthetic organic polymers as well as mixtures of the same in the form of aqueous dispersions. The dispersions can be spread on a base to form a uniform layer which results in a water-resistant film after drying. The dry films have a thickness of 10 μm to 500 μm, preferably of 30 to 200 μm. The film can be used together with the base as a support or it can be mounted on another support for the detection reaction. Although the reagents required for the detection reaction are normally added to the dispersion used to produce the open films, it may also be advantageous to impregnate the final film with the reagents after its production. It is also possible to preimpregnate the filling materials with the reagents. Which reagents can be used to determine a particular analyte are known to a person skilled in the art. This does not have to be elucidated in more detail here.

An additional example of a preferred detection layer according to the invention is a film layer as described in WO-A-92 15 879. This layer is produced from a dispersion or emulsion of a polymeric film former which additionally contains a pigment, a swelling agent and the detection reagent in a homogeneous dispersion. Polyvinyl esters, polyvinyl acetates, polyacrylic esters, polymethacrylic acid, polyvinylamides, polyamides and polystyrene are particularly suitable as polymeric film formers. In addition to homopolymers mixed polymers e.g. of butadiene, styrene or maleic acid ester are also suitable. Titanium dioxide is a particularly suitable pigment for the film. The swelling agent used should have particularly good swelling properties and methyl-vinyl ether maleic acid copolymer is particularly recommended. It is left to a person skilled in the art to decide which reagent to use to determine a particular analyte.

In a diagnostic test carrier according to the invention it is particularly preferable to use a test field as a detection layer which is composed of two layers. This test field comprises a transparent foil on which a first and a second film layer are applied on top of each other in this order. It is essential that the first layer located on the transparent foil scatters light considerably less in a wet state than the overlying second layer. The non-coated side of the transparent foil is referred to as the detection side and the side of the second layer which is opposite to the side of the second layer which lies on top of the first is referred to as the sample application side.

The film layers are produced from dispersions or emulsions of polymeric film formers. Dispersion film formers contain microscopic polymer particles which are insoluble in the carrier liquid (usually water) and which are dispersed in very fine dispersion in the carrier liquid. If the liquid is removed by evaporation during film formation the particles approach one another and finely touch. The large forces which occur in this process and a gain in surface energy which accompanies the film formation results in growth of the particles to form a substantially closed film layer. Alternatively it is also possible to use an emulsion of a film former in which this is dissolved in a solvent. The dissolved polymer is emulsified in a carrier liquid which is immiscible with the solvent.

Polyvinyl esters, polyvinyl acetates, polyacrylic esters, polymethacrylic acid, polyvinylamides, polyamides and polystyrene are particularly suitable as polymeric film formers. In addition to homopolymers mixed polymers e.g. of butadiene, styrene or maleic acid ester are also suitable.

In the test field the two said film layers are located on a transparent foil. Plastic foils which come especially into consideration for this are those which are liquid impermeable. Polycarbonate foil has proven to be particularly preferred.

The two film layers can be produced as coating compounds which contain the same polymeric film former or they can be produced from coating compounds which contain different polymeric film formers.

If there are special test functions and/or test conditions such as in the determination of glucose in whole blood it is expedient to form the layers such that, apart from a good erythrocyte separation, they also have optical features which facilitate the observation of the detection reaction and the exactness of the assessment and improve the technical measurement of the measurement.

For this the first layer expediently contains a swelling agent and optionally a weak light-scattering filling material, the second layer contains a swelling agent and at least one strongly light-scattering pigment. In addition the second layer can also contain non-porous filling materials and porous filling materials such as kieselguhr in low amounts without becoming permeable for erythrocytes.

By adding a good swelling agent (i.e. a substance which increases its volume by uptake of water) one not only obtains layers which are relatively rapidly penetrated by sample liquid but which, despite this opening effect of the swelling agent, have good erythrocyte and additionally also blood pigment separation properties. The swelling properties should be so good that for a test for which the rate of colour formation—such as for example a glucose detection reaction—largely depends on the penetration of the sample liquid through the layer, the optically detectable reaction is measurable after a maximum of one minute. Xanthan gum and methyl vinyl ether maleic acid copolymers have proven to be particularly suitable swelling agents.

Kieselguhr is also referred to as diatomaceous earth. These are deposits formed from the silicic acid skeletons of diatom species which are mined at different sites. The preferably used kieselguhr has an average particle diameter of 5-15 μm and these values were determined with a laser granulometer type 715 which is distributed by the Pabisch Company, Munich, Germany.

The amount of the strongly light-scattering pigment of the second layer is at least 25% by weight relative to the dry and ready-to-use double layer of the test field. Since the weakly light-scattering filling materials and the strongly light-scattering pigments are mainly responsible for the optical properties of the film layers, the first and the second film layer have different filling materials and pigments.

The first film layer should either contain no fillers or fillers whose refractive index is close to the refractive index of water. Precipitated silicic acids, silicon dioxide, silicates and aluminium silicate have proven to be particularly suitable for this. A sodium aluminium silicate with the trade name Transpafill® is particularly preferred.

The second layer should scatter light as strongly as possible. Ideally the refractive index of the pigments in the second film layer should be at least 2.5. Therefore titanium dioxide is preferably used. Particles with an average diameter of about 0.2 to 0.8 μm have proven to be particularly advantageous. Readily processible titanium dioxide types in the anatase modification are quite especially preferred.

Reagent systems for the detection of particular analytes by colour formation are known to a person skilled in the art. It is possible that all components of the reagent system are located in one film layer. It is, however, also possible that the components of the reagent system are divided between the two film layers. Advantageously the colour forming reagent system is at least partly located in the first film layer.

Colour formation is understood in the scope of the present invention not only to mean the transition from white to coloured but also any colour change whereby of course those colour changes are particularly preferred which are associated with the largest possible shift of the maximum absorption wavelength ($\lambda$ max).

In order to optimize the test field in the diagnostic test carrier according to the invention it has proven to be particularly advantageous when both film layers contain a non-haemolyzing wetting agent. Neutral i.e. non-charged wetting agents are particularly suitable for this. N-octanoyl-N-methyl-glucamide is quite especially preferred. Additionally other wetting agents can be contained in the film layers which promote the homogeneity of the coatings such as sodium N-methyl-N-oleoyl-taurate.

In order to produce a test field of a diagnostic test carrier according to the invention the respective film layers are each produced successively from a homogenous dispersion of the said components. For this the transparent foil is used as a base to shape the coating compound for the first film layer. After the coating compound for the first film layer has been applied with a certain layer thickness, the layer is dried. Afterwards the coating compound for the second layer is also applied in a thin coating layer and dried. After drying the thickness of the first and second film layer should be together no more than 0.2 mm, preferably no more than 0.12 mm and particularly preferably no more than 0.08 mm.

The attachment can be carried out by methods known to a person skilled in the art from test carrier technology. For example the attachment can be by means of hot-melt adhesive or hardening cold-setting adhesive. In this connection a spotted or rastered glueing is advantageous since this especially facilitates capillary active liquid transport. Double-sided adhesive strips have also proven to be advantageous. However, in all cases it is important that the attachment of the overlay on the support layer is such that a capillary-active liquid transport is possible from the detection layer into that part of the overlay which is attached to the support layer. This capillary-active liquid transport must be especially possible when the detection layer is saturated with liquid. Adhesive tapes containing natural or synthetic rubber have proven to be particularly suitable for the manufacture. It is particularly advantageous when the agent that is used to attach the overlay to the support layer has approximately the same thickness as the detection layer(s). It then serves as a spacer in order to keep the entire overlay according to the invention on one continuous plane even outside the region of the detection layer(s).

In order to determine the analyte to be detected in the sample liquid, the detection layer but at least the reaction zones thereof i.e. the regions of the detection layer(s) which carry reagent which can be observed for signal formation and measured, are visible through the support layer in the diagnostic test carrier according to the invention. As already described above this can be achieved by having a transparent support layer. It is, however, also possible that the support layer has a perforation which is covered by the detection layer or the detection layers. The detection layer or the detection layers but at least the reaction zones of the detection layers are then visible through the perforation. In a preferred embodiment of the diagnostic test carrier according to the invention there is a hole in the support layer below the detection layer through which the detection layer or a reaction zone can be observed. The hole has a somewhat smaller diameter than the smallest linear extension of the detection layer so that the detection layer rests on the support layer outside the hole and can be attached there. Advantageously the detection layer is adequately attached by double-sided adhesive tapes arranged on both sides and by the overlay according to the invention lying over the detection layer and its attachment to the support layer. However, the detection layer itself is also preferably attached to the support layer by at least a thin adhesive tape.

It is, however, also possible to observe several reaction zones of a detection layer through a hole.

The perforation of a diagnostic test carrier according to the invention can also be composed of two or several holes which can be used to determine the analyte (one or several analytes). Several detection layers or only one detection layer with several reaction zones can be arranged above the holes so that through each hole one detection layer or one reaction zone can be observed. It is, however, also possible that several reaction zones can be observed through one hole.

An inert cover made of sample-impermeable, usually water-impermeable and non-absorbent material can be arranged over the overlay according to the invention of the diagnostic test carrier according to the invention in such a manner that is covers the region of the overlay outside the detection layer. Ideally the cover also extends into the region of the detection layer but, however, in any case leaves a middle part of the overlay according to the invention which covers the detection layer free. This free part of the overlay is referred to as the sample application site.

Plastic foils have proven to be particularly advantageous as a cover. If the cover and the overlay according to the invention have different colours, for example white and yellow or white and red, then this clearly indicates the site at which the sample liquid to be examined should be applied.

The direction i.e. which end of a diagnostic test carrier according to the invention should be placed or inserted into a measuring instrument can also be made evident on the cover for example by printing on one or several arrows.

A sample application site can be accessed through a cover particularly simply by means of two strip-shaped plastic foils which leave a strip-like region of the overlay according to the invention covering the detection layer free. If 2 or more sample application sites are intended then three or more strip-shaped plastic foils have to be used. The foils used for the cover are attached to the overlay according to the invention and optionally to the support layer. Hot-melt adhesives which are preferably applied in spots or in a pattern on the support layer or on the underside of the cover are suitable for such an attachment or adhesive tapes if the foils are not self-adhesive. The sample application site is preferably located above the perforation in the support layer through which a signal generation on the detection layer can be observed.

The present invention also concerns a process for the production of a diagnostic test strip in which single or multilayer detection fields are mounted on a support which is optionally transparent or provided with inspection openings and the detection fields are covered with a functional overlay which rests loosely on the test fields and is attached at the sides of the test fields and optionally a further inert cover which only leaves the sample application site free is additionally mounted which is characterized in that a flat-shaped overlay element or several overlapping flat-shaped overlay elements that together form the overlay are attached to the test strip next to the test field(s) in such a way that a part of their surface covers the test field(s) and can move freely relative to the test field(s) in the direction of curvature produced when the object is bent.

Flat-shaped overlay elements are preferably used in this process which are composed of one of the above-mentioned preferred textile materials.

It is particularly preferable to use flat-shaped overlay elements which are hydrophilized with an N-acyl-N-alkyl-glycinate of formula I.

In order to carry out a method for the determination of an analyte in a liquid sample with the aid of a diagnostic test carrier according to the invention the sample liquid is applied to the side of the overlay which faces away from the detection layer and ideally sufficient so that the liquid which passes through the overlay according to the invention completely saturates the detection layer. Body fluids such as blood, plasma, serum, urine, saliva etc. come into particular consideration as the sample liquid. Blood or liquids derived from blood such as plasma or serum and urine are particularly preferred sample liquids. Then if the analyte to be determined is present a signal can be detected in the detection layer. Such a signal is advantageously a colour change which is understood as colour formation, loss of colour as well as colour transition. The intensity of the colour change is a measure for the amount of analyte in the examined liquid sample. It can be evaluated visually or quantitatively with the aid of an instrument, usually by reflection photometry, in which case calibration curves created in preliminary experiments can be used. Alternatively the content of analyte can be displayed directly by means of the instrument's software.

A major advantage of the diagnostic test carrier according to the invention is that it is not necessary to apply a predetermined volume of a sample liquid on the test carrier. Excess liquid is not conducted to the detection zone but remains above the application gap. This is a very important aspect especially when examining blood or samples derived from blood such as plasma or serum.

Even if blood is applied directly from the finger pad the test strip according to the invention proves to be self-dosing. It removes ca. 5 µl from the blood drop on the finger pad the remainder remains on the finger.

Covering parts of the overlay according to the invention and thus marking the sample application site ensures that liquid can only reach the detection layer at the optimal site for this. In combination with the detection layer which only takes up a small amount of liquid and nevertheless ensures an intensive signal generation, this ensures that reliable analyte determinations are possible even with very small sample volumes. Since the test carrier according to the invention is only composed of a few components which can be simply and rapidly assembled, it is very cheap to manufacture.

In the embodiments of the present invention described above the whole area of the attachment region of the overlay elements is attached to the carrier preferably by means of spacers. However, as already stated above an attachment over the whole area is not necessary at all. Rather a single and preferably two attachment points which are located in the attachment region of the overlay element are in principle sufficient. In such an embodiment the attachment points of the overlay element in the attachment region can be located on each edge of the overlay element which extends in the direction of curvature. The part of the attachment region between the edges has in contrast no attachment points.

Figure 11:
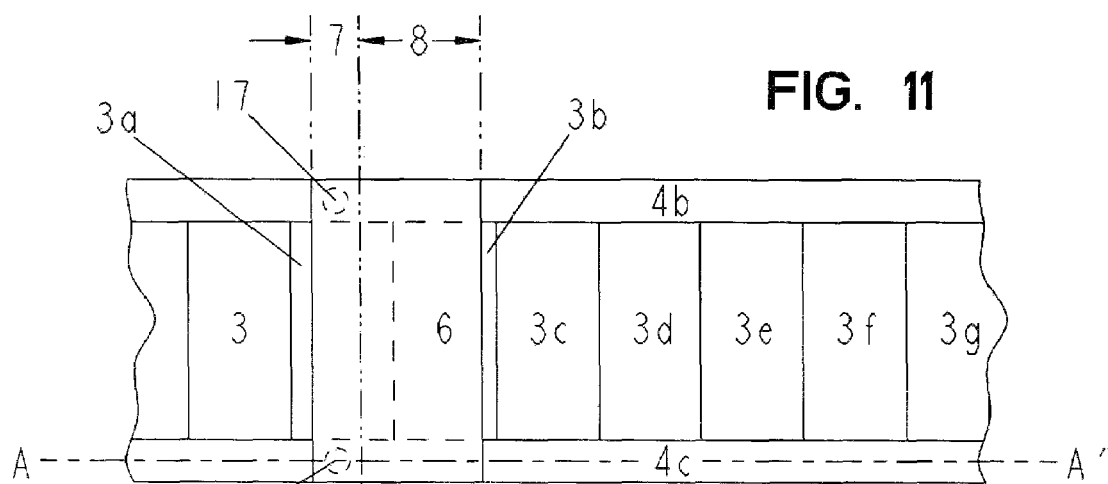
Figure 12:
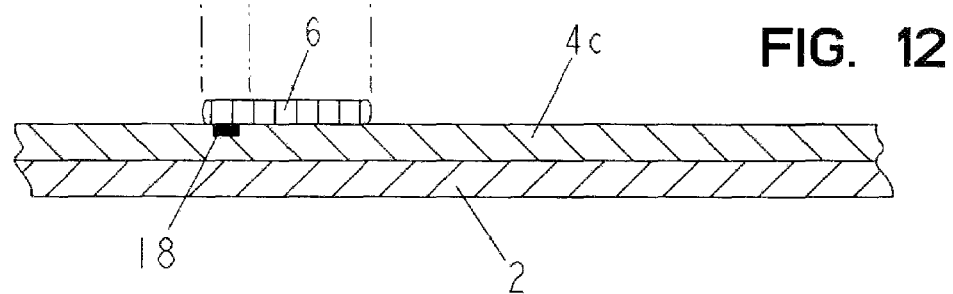

FIG. 11 shows a top-view of a section of a test strip, FIG. 12 shows a transverse section along the cut line A-A' of this object. The strip has an uninterrupted sequence of detection fields (3 to 3g) which extend in the direction of the longitudinal axis of the test strip. Spacer strips (4b and 4c) also extend on both sides of the detection zones in the longitudinal direction of the test strip on which the inventive overlay element (6) covering a partial region of the detection layer is attached at points 17 and 18 of its attachment region (7) but rests loosely thereon in the slidable region (8).

It is expedient to choose this type of attachment when it is necessary to cover a elongate partial area of the object by several shingle-like overlapping overlay elements arranged one behind the other in the same direction or back to back in the direction of curvature. FIGS. 13 and 14 illustrate this embodiment of the invention.

FIG. 13 shows a top-view of a section of a test strip, FIG. 14 shows a transverse section along the cut line A-A' of this object. Like that shown in FIG. 11 the strip has an uninterrupted sequence of detection fields which are not shown in FIG. 13 for reasons of clarity which extend in the direction of the longitudinal axis of the test strip. Spacer strips (4b and 4c) extend also in the longitudinal direction of the test strip on which a series of shingle-like overlapping overlay elements according to the invention (6a to 6f) covering the detection layer is attached at points (17 to 17d) and (18 to 18d).

Such an embodiment of test strips and test leaves can for example be used for a fine determination of the pH value by means of a large series of different indicator fields to which the sample is applied in the form of an application line running in the longitudinal axis of the strip.

This embodiment shows that the principle of the one-sided attachment of the overlay elements lends itself to manifold variation. These variations are also part of this invention.

The following application examples illustrate the manufacture of a test strip according to the invention and its use.

EXAMPLE 1

Manufacture of a diagnostic test carrier according to the invention containing two detection fields for the determination of glucose at a low and high concentration.

A test carrier according to FIGS. 8, 9 and 10 is manufactured by the following process steps:

A 10 mm wide double-sided adhesive tape (polyester support and synthetic rubber adhesive) is mounted parallel on a strip-shaped 50 mm wide titanium dioxide-containing polyester support layer at a distance of 18.6 mm and to its left edge (measured from the left edge of the adhesive tape). Three holes are punched out of this sandwich at a distance of 6 mm i.e. a positioning hole and two inspection and measuring holes whose centres lie on a straight line perpendicular to the longitudinal axis of the carrier strip. The first hole, the positioning hole, is circular, has a diameter of 2.6 mm and its centre is at a distance of 4 mm from the left edge of the carrier strip. The second hole is also round with a diameter of 4 mm, the third hole is rectangular with an edge length of 3 mm in the longitudinal direction of the strip and 4 mm in the cross direction. Both the second and third hole have a centre to centre distance of 5.1 mm on the adhesive tape, the centre of the second hole is at a distance of 21 mm from the left edge of the carrier strip.

Afterwards the protective paper on the double-sided adhesive tape is pulled off.

The procedure for the production of the first detection layer which is composed of 2 film layers is as follows:

A. The following components are added together in a beaker as pure substances or in the form of stock solutions in the following composition and mixed by stirring:

water: 820.0 g
citric acid-1 hydrate: 2.5 g
calcium chloride-2-hydrate: 0.5 g
sodium hydroxide: 1.4 g
xanthan gum: 3.4 g
tetraethylammonium chloride: 2.0 g
N-octanoyl-N-methylglucamide: 2.1 g
sodium N-methyl-N-oleoyl-taurate: 0.29 g
polyvinylpyrrolidone (MW 25000): 3.5 g
Transpafill (sodium-aluminium silicate): 62.1 g
polyvinylpropionate dispersion (50% by weight in water): 60.8 g
Bis-(2-hydroxyethyl)-(4-hydroxyiminocyclohexa-2,5-dienylidine)-ammonium chloride: 1.2 g
2,18-phosphomolybdic acid hexasodium salt: 16.1 g pyrroloquinoline quinone: 32 mg
glucose dehydrogenase rec. from Acinetobacter calcoaceticus, 1.7

MU EC 1.1.99.17: (2.4 g)
1-hexanol: 1.6 g
1-methoxy-2-propanol: 20.4 g

The total composition is adjusted with NaOH to a pH of ca. 6 and then coated on a 125µ thick polycarbonate foil at a weight per unit area of 89 g/qm and dried.

B. The following components are added together in a beaker as pure substances or in the form of stock solutions in the following composition and mixed by stirring:

Water: 579.7 g
sodium hydroxide: 3.4 g
Gantrez (methyl vinyl ether maleic acid copolymer): 13.8 g
N-octanoyl-N-methyl-glucamide: 3.6 g
sodium N-methyl-N-oleoyl-taurate 0.25 g
tetraethylammonium chloride: 9.7 g
polyvinylpyrrolidone (MW 25000): 20.2 g
titanium dioxide: 177.1 g
kieselguhr: 55.3 g
polyvinylpropionate dispersion (50% weight in water): 70.6 g
2,18-phosphomolybdic acid hexasodium salt: 44.3 g
potassium hexacyanoferrate (III): 0.3 g
1-hexanol: 1.6 g
1-methoxy-2-propanol: 20.4 g The total composition is adjusted with NaOH to a pH of ca. 6 and then coated on a polycarbonate foil as described under A. at a weight per unit area of 104 g/qm and dried. After drying the layer thickness is 60 µm.

The second detection layer which is also composed of 2 film layers is manufactured as follows:

A. The following components are added together in a beaker as pure substances or in the form of stock solutions in the stated amounts and mixed by stirring:

Water: 820.0 g
citric acid-1-hydrate: 2.5 g
calcium chloride-2-hydrate: 0.5 g
sodium hydroxide: 1.4 g
xanthan gum: 3.4 g
tetraethylammonium chloride: 4.22 g
N-octanoyl-N-methyl-glucamide: 2.1 g
sodium N-methyl-N-oleoyl-taurate: 0.29 g
polyvinylpyrrolidone (MW 25000): 3.5 g
Transpafill (sodium aluminium silicate): 62.1 g
polyvinylpropionate dispersion (50% by weight in water): 60.8 g
N-(4-nitrosophenyl)-N'-carboxymethyl-piperazine: 1.0 g
2,18-phosphomolybdic acid hexasodium salt: 20.9 g
pyrroloquinoline-quinone: 32 mg
glucose dehydrogenase rec. from Acinetobacter calcoaceticus: 1.7 MU
(EC 1.1.99.17): (2.4 g)
1-hexanol: 1.6 g
1-methoxy-2-propanol: 20.4 g The total composition is adjusted with sodium hydroxide solution to a pH of ca. 6.0 and then coated on a 125 µm thick polycarbonate foil at a weight per unit area of 89 g/m² and dried.

B. The following components are added together in a beaker as pure substances or in the form of stock solutions in the stated amounts and mixed by stirring:

water: 579.7 g
sodium hydroxide: 3.4 g
Gantrez (methyl vinyl ether maleic acid copolymer): 13.8 g
tetraethylammonium chloride: 6.71 g
N-octanoyl-N-methyl-glucamide: 2.74 g
sodium N-methyl-N-oleoyl-taurate: 0.25 g
polyvinylpyrrolidone (MW 25000): 15.6 g
titanium dioxide: 136.7 g
polyvinylpropionate dispersion (50% by weight in water): 54.6 g
N-(4-nitrosophenyl)-N'-carboxymethyl-piperazine: 1.51 g
2,18-phosphomolybdic acid hexasodium salt: 33.13 g
potassium hexacyanoferrate (III): 0.28 g
1-hexanol: 1.6 g
1-methoxy-2-propanol: 20.4 g The total composition is adjusted with sodium hydroxide solution to a pH of ca. 6.0 and then coated on a polycarbonate foil coated as described in A at a weight per unit area of 102 g/m² and dried. After drying the layer thickness is 55 µm.

The foil side of a 5 mm wide strip of each of the detection layers prepared in this manner is glued and fitted accurately on the support layer on the punched double-sided adhesive tape in such a manner that the strips are directly adjacent to one another.

Double-sided adhesive tape having the thickness of the detection strips are glued as spacers onto the carrier foil directly adjacent to and on both sides of the detection layers. In the present example one spacer is 6 mm and the other is 9 mm wide. Afterwards the protective foil of the two double-sided adhesive tapes is pulled off.

Then a 10 mm wide strip of a monofilament polyester fabric (type PE38 HC from the ZBF Mesh-Technology, Company, Rüschlikon, Switzerland) impregnated with a wetting agent is placed on the 9 mm wide spacer in such a manner that the cut edge of the fabric strip overhangs the borderline between the detection strips by 0.5 to 0.6 mm and is fixed by pressing. Subsequently a 10 mm wide strip of the same polyester fabric is placed on the 6 mm wide spacer in such a manner that it overlaps the cut edge of the first fabric strip by 1 to 1.2 mm and is fixed by pressing.

Afterwards two single-sided adhesive tapes (PVC support and natural rubber adhesive) are glued as covers onto both sides of the construction in such a manner that a gap of 2 to 2.5 mm remains uncovered symmetrical to the borderline of the detection strips. The tapeware is thus finished.

The tapeware is cut into 6 mm wide test carriers such that the measuring and inspection holes and the positioning hole lie in the middle of the test carrier.

EXAMPLE 2

Example 1 is repeated except that the monofilament polyester fabric type PE38 HC used for the overlay according to the invention is impregnated with sodium N-oleoyl-sacosinate as the wetting agent. The amount of wetting agent on the fabric is 0.25% by weight relative to the weight of the fabric before impregnation.

EXAMPLE 3

Test strips are manufactured according to example 1 which have the same detection layers in both detection fields. The polyester fabric type PE 38 HC impregnated with 0.25% by weight sodium N-oleoyl-sarcosinate used in example 2 is used as a spreading layer. The strips are inserted into a GLUCOTREND instrument set up to measure both test fields simultaneously during which they are subjected to a slight bending in order to fix them in their measurement position.

The strips are spotted with increasing volumes of EDTA venous blood containing 102 mg/dl glucose. For each volume 5 series of 10 test strips were measured (n=5, N=50). From this 5 CV values were calculated for each volume. (The CV value is defined as the relative standard deviation $CV$=standard deviation/mean and is stated in %)

The following table shows the medians of the measured results and the medians of the CV values of the 5 series per volume:

|  | Field 1 | | Field 2 | |
| --- | --- | --- | --- | --- |
| Volume | median of the measured value [mg/dl] | median of the CV value [%] | median of the measured value [mg/dl] | median of the CV value [%] |
| 3 μl | error* | — | 63.4** | 9.3 |
| 4 μl | 100 | 2.5 | 102 | 2.7 |
| 5 μl | 102 | 2.3 | 103 | 2.6 |
| 10 μl | 101 | 2.2 | 102 | 2.7 |
| 15 μl | 103 | 2.4 | 102 | 2.7 |

Remarks:
*An inhomogeneous reaction coloration on field 1 is detected by the 2-LED optics of the instrument (described in EP-A-819 943). The instrument therefore only gives an error message but no measured value.
**Field 2 is only illuminated with one LED so that an inhomogeneous coloration of the test field is not detected. Consequently the CV value is greatly increased. However, the instrument can give the error message "different intensities of the reaction colour of both fields" by comparing both test fields. This function was switched off during the measurement carried out in this case.

The experiments show that both test fields indicate the same colour i.e. the same glucose concentration above a sample volume of 4 μl. This demonstrates the excellent spreading action of the overlay according to the invention over both measurement fields. With higher sample volumes the value does not change since the excess sample material remains above the application gap. With smaller volumes the wetting and hence also the coloration of the two reaction zones is incomplete which can be detected by the 2 LED optics of field 1. Appropriate software measures can prevent such measurements from leading to a display of (false-negative) values. Instead an error message is displayed which indicates to the user that the sample volume is too low.

The invention claimed is:

1. A method, comprising:
   assembling a diagnostic test strip, wherein said assembling includes
   providing a generally flat flexible base layer with a test field,
   attaching first and second spacers to the base layer bordering the test field,
   attaching and positioning first and second functional overlays to the first and second spacers, respectively, each overlay having an attachment region attached to the respective spacer and a cover region overlying the test field, and
   wherein the attaching and positioning first and second functional overlays includes overlapping a first portion of the cover region of the first functional overlay with a second portion of the cover region of the second functional overlay; and
   maintaining contact between the cover regions and the test field when the diagnostic test strip is bent toward the side on which the first and second functional overlays are located to substantially prevent outward deformation of the cover regions away from the first and second functional overlays.

2. The method of claim 1, further comprising:
   attaching a first protective cover to the base layer to cover at least the attachment region of the first functional overlay, and
   attaching a second protective cover to the base layer to cover at least the attachment region of the second functional overlay.

3. A method, comprising:
   assembling a diagnostic test strip, wherein said assembling includes
   providing a generally flat flexible base layer with a first and second test field,
   attaching first and second spacers to the base layer bordering the first and second test fields,
   attaching a first functional overlay to the base layer, the first overlay having an attachment region and a cover region, the attachment region attached to the first and second spacers, the cover region positioned over the first test field,
   attaching a second functional overlay to the base layer, the second overlay having an attachment region and a cover region, the attachment region attached to the first and second spacers, the cover region positioned over the second test field, and
   overlapping a portion of the cover region of the second functional overlay with the attachment region of the first functional overlay.

4. The method of claim 3, further comprising:
   maintaining contact between the cover regions and the first and second test fields when the diagnostic test strip is bent toward the side on which the first and second functional overlays are located to substantially prevent outward deformation of the cover regions away from the first and second test fields.

5. A method, comprising:
   assembling a diagnostic test strip, wherein said assembling includes
   attaching first and second spacers to a base layer, the base layer having a test field positioned between the first and second spacers;
   selectively securing a first functional overlay to the first spacer and the test field, the first functional overlay having an attachment region and a cover region, the attachment region attached to the first spacer, the cover region placed on the test field;
   selectively securing a second functional overlay to the second spacer and the test field, the second functional overlay having an attachment region and a cover region, the attachment region attached to the second spacer, the cover region placed on the test field; and
   overlapping a first portion of the cover region of the first functional overlay with a second portion of the cover region of the second functional overlay, wherein the first functional overlay is slidable over the second functional overlay.

* * * * *